United States Patent [19]
Taheri

[11] Patent Number: 5,948,017
[45] Date of Patent: Sep. 7, 1999

[54] MODULAR GRAFT ASSEMBLY

[76] Inventor: Syde A. Taheri, 268 Dan Troy, Williamsville, N.Y. 14221

[21] Appl. No.: 08/946,748

[22] Filed: Oct. 12, 1997

[51] Int. Cl.$^6$ .............................. A61F 2/06; A61F 2/02; A61M 25/09
[52] U.S. Cl. .................................... 623/1; 623/2; 623/11; 623/12; 606/194; 606/195; 606/198; 606/200
[58] Field of Search .............................. 623/1, 2, 11, 12; 606/194, 195, 198, 200

[56] References Cited

U.S. PATENT DOCUMENTS

| | | | |
|---|---|---|---|
| 5,456,694 | 10/1995 | Marin et al. | 606/198 |
| 5,800,521 | 9/1998 | Orth | 623/1 |
| 5,843,162 | 12/1998 | Inoue | 623/1 |

*Primary Examiner*—Mickey Yu
*Assistant Examiner*—Choon P. Koh
*Attorney, Agent, or Firm*—Hodgson, Russ, Andrews, Woods & Goodyear LLP

[57] ABSTRACT

An apparatus for engrafting a blood vessel comprising: a plurality of strings, a tubular graft having a central lumen, wherein the plurality of strings are removably attached to the tubular graft, the graft is removably positioned at least partially within a restraining means, such as a sheath introducer, a guide wire with an attachment means for attachment of the plurality of strings, one or more stents for deployment within the graft, and a means for deploying the stents within the graft.

23 Claims, 15 Drawing Sheets

MODULAR GRAFT ASSEMBLY

FIELD OF THE INVENTION

The present invention relates to a blood vessel engrafting system for repairing aneurysms and more particularly to a modular graft system for repairing aortic aneurysms by building a spring loaded graft within a blood vessel via percutaneous entry.

BACKGROUND OF THE INVENTION

An aortic aneurysm is a very common deteriorating disease typically manifested by a weakening and expansion of the aorta vessel wall at a region between the aorta-renal junction and the aorta-iliac junction. An aneurysm affects the ability of the vessel lumen to conduct fluids, and may at times be life threatening, for instance, when rupture of the vessel wall occurs. A standard treatment for repairing an aneurysm is to surgically remove part or all of the aneurysm and implant a replacement prosthetic section into the vessel. Such surgery, however, is generally postponed until the aneurysm has grown to a diameter greater than five centimeters. With aneurysms over five centimeters in diameter, the risk of complications is greater than the risks inherent in surgical excision and grafting of the aneurysm. Consequently, aortic aneurysms measuring greater than five centimeters in diameter, and those showing rapid increase in size, are generally surgically engrafted as a matter of course, before rupture occurs.

The standard procedure for repairing an aortic aneurysm requires one or two days of preparing the large and small intestines prior to hospitalization. The operation itself generally takes one to three hours to perform, and necessitates several units of blood for transfusion. The patient commonly remains hospitalized for several days following surgery, and requires as much as three months recuperation time before returning to work.

Moreover, there remains a significantly high rate of mortality and morbidity associated with the standard procedure. The mortality rate is as high as 8%, while the morbidity rate includes incident complications such as blood loss, respiratory tract infections, wound infections, graft infections, renal failure, and ischemia of the bleeding intestine. The mortality and morbidity rates for this type of major surgery are also often influenced by the fact that the typical aortic aneurysm patient is elderly and therefor less able to withstand major surgery, including anesthesia.

Other treatments for repairing an aneurysm involve deploying a graft device at the aneurysm site via a catheter traveling through a femoral artery. Conventional tubular aortic replacement sections, however, are generally considerably larger in diameter than the femoral artery and therefore cannot be inserted through the femoral artery lumen to the site of the aneurysm.

Even in the more advanced aortic graft assemblies which enable percutaneous deployment and placement of a spring loaded graft for a non-surgical correction of an aortic aneurysm, the required entry profiles require at least 10–12 FR. This is the case since these graft systems are comprised of graft material, two or more spring stents, a balloon catheter, a sheath introducer, and plunger at a minimum, for deployment of the graft.

Thus, there exists a need for a treatment for aneurysms utilizing a system enabling deployment and placement of an aortic graft which is much smaller thus able to facilitate a much smaller entry profile.

SUMMARY OF THE INVENTION

The present invention is comprised of an apparatus for engrafting a blood vessel comprising: a plurality of strings, a tubular graft having a central lumen, wherein the plurality of strings are removably attached to the tubular graft, the graft is removably positioned at least partially within a restraining means, such as a sheath introducer, a guide wire with an attachment means for attachment of the plurality of strings, one or more stents for deployment within the graft, and a means for deploying the stents within the graft.

DETAILED DESCRIPTION OF THE PREFERRED EMBODIMENTS

The nature and mode of operation of the present invention will now be more fully described in the following detailed description of a preferred embodiment and alternative embodiments to be read together with the accompanying drawing figures.

The term distal is used in this application. It refers to a position relative not to the heart, but to the respective point of entry into the blood vessel. Furthermore, the terms proximal and proximate are used in this application. These terms refer to a position relative not to the heart, but to the respective point of entry. Thus, with respect to an apparatus, the end closer to the point of entry would be the proximate end, and the end farthest from the point of entry would be the distal end.

Figure 1A:
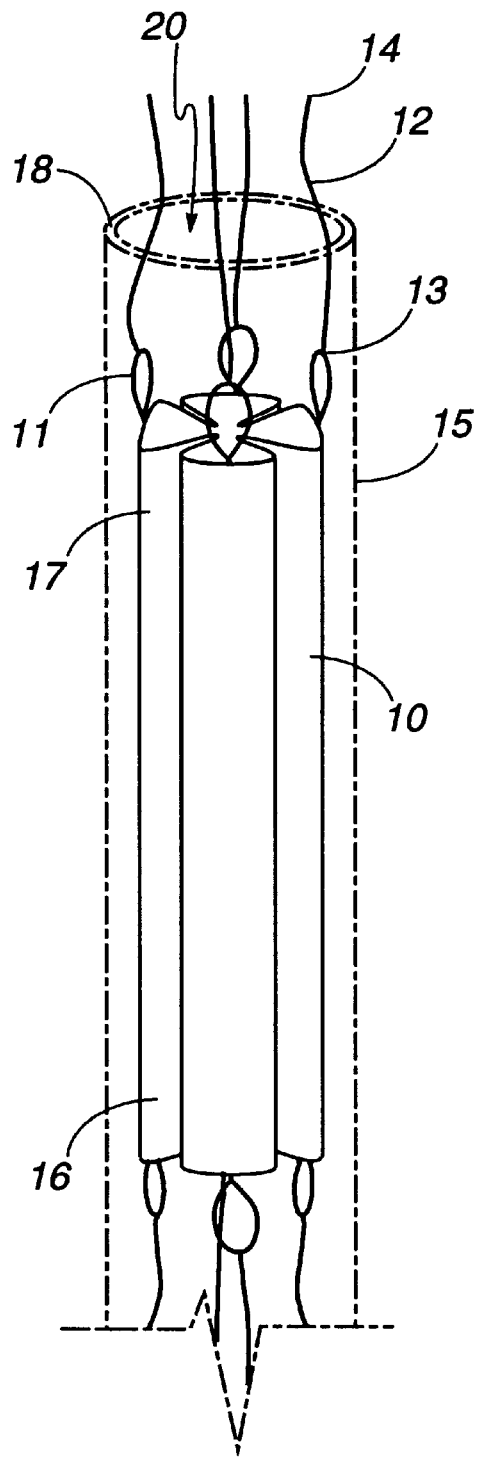
FIG. 1A is a perspective view of the graft of the inventive assembly loaded within a sheath introducer.
Figure 1B:
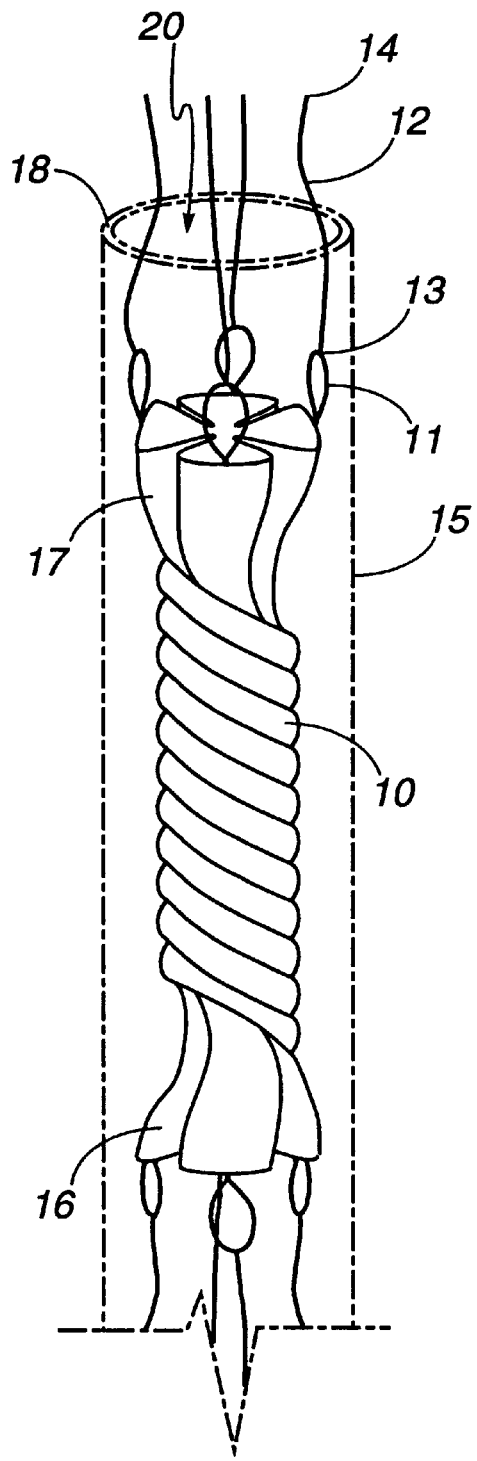
FIG. 1B is a perspective view of the graft of the inventive assembly loaded within a sheath introducer in a twisted position.

As shown in FIG. 1, the present invention is comprised of a graft 10, preferably Dacron, of a tubular shape when in an expanded position, and capable of being folded or twisted for loading into a sheath introducer 15. Graft 10 may have even end portions as shown in FIGS. 1A, 1B, 6A, 6B, 7, 8, 9, and 10 or may have finger-like end portions as shown in the remaining graft drawings. Graft 10 is further comprised of a first end 16 and a second end 17, each end having a plurality of loops 11, preferably four loops at each side.

Sheath introducer 15 is comprised of a standard material such as plastic or any other substantially flexible material, and contains a distal end 18 and a proximal end (not shown), each end containing an opening 20.

The present invention is further comprised of a plurality of strings 12 for temporary attachment to the loops 11 of graft 10. In particular, prior to loading of graft 10 into sheath introducer 15, strings 12 are temporarily attached to loops 11 by passing one end of each string 12 through a loop 11 pulling each end of each string upward and away from loops 11 such that a middle portion 13 of each string 12 is folded over each loop 11.

Figure 2A:
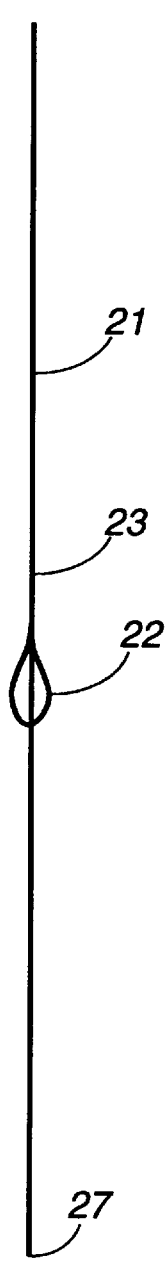
FIG. 2A is a perspective view of the first embodiment of the guide wire of the present invention.
Figure 2B:
FIG. 2B is a second embodiment of the guide wire of the present invention.
Figure 2C:
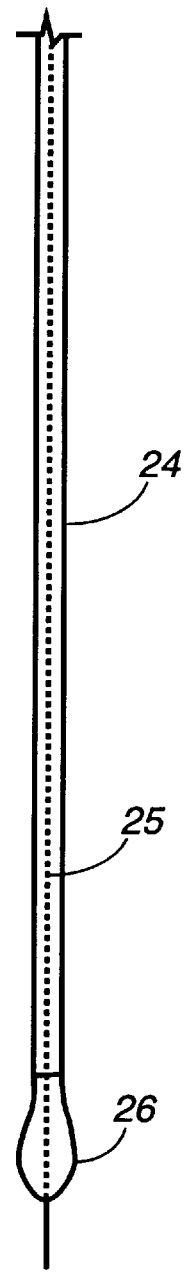
FIG. 2C is a third embodiment of the guide wire of the present invention.
Figure 3A:
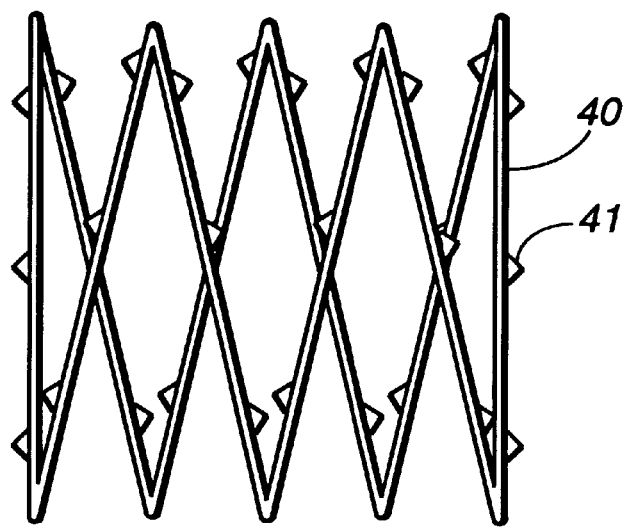
FIG. 3A is a perspective view of the stent of the present invention.
Figure 3B:
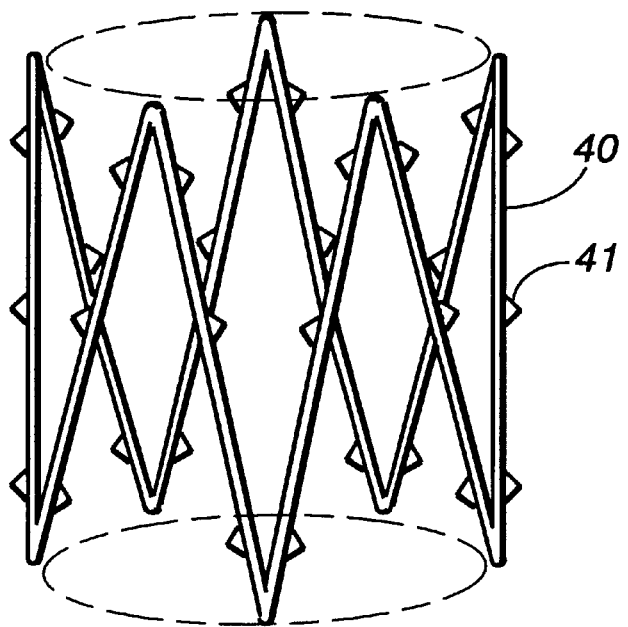
FIG. 3B is a perspective view of the stent of the present invention.

As displayed in FIG. 2a, the present invention is further comprised of a guide wire 21 for guiding string ends 14 from a point of entry 30 into the femoral artery 31 to a point of entry 32 in the brachial artery 33. Guide wire 21 is long enough to extend from point of entry 32 through point of entry 30 with plenty of room on each side for manipulation thereof. Guide wire 21 is preferably about 0.38 millimeters in diameter and is comprised of a somewhat flexible material such as thin metal or plastic, having an attachment means 22 in a middle portion 23 thereof. In operation, string ends 14 are temporarily affixed to attachment means 22, preferably a ring, for passage from the femoral artery 31 to the brachial artery 33 and out the original point of entry 32.

Guide wire 21a is an alternative embodiment having attachment means 22a at a distal end 23a thereof. Guide wire 24 is yet another embodiment and is comprised of a central lumen 25 in fluid communication with a tip balloon 26. In operation, tip balloon 26 is inflated within the second end 17 of graft 10 for temporary attachment and passage from the femoral artery 31 through the point of entry of the brachial artery 32.

As shown in FIGS. 3A, 3B, 8, 9, 10, the present invention is further comprised of a stent delivery system having one or more stents 40, a sheath introducer 45, and balloon catheter 50 and a plunger (not shown).

A stent 40 is comprised of a wire formed in an endless series of straight sections joined by bends; a zig-zag configuration. Stent 40 is further comprised of a plurality of spikes 41, for more securely affixing stent 40 within graft 10 and blood vessel 34. Spikes 41 line the outer surface of stent 40, or more particularly the surface of the stent which is in contact with graft 10 after deployment thereof. Spikes 41 are comprised of a rigid material, such as metal or plastic, and are preferably cone shaped. Furthermore, stent 40 is comprised of a material such as metal which is deformable and capable of returning to its original shape; preferably a shape memory alloy having stress-induced martensite characteristics, such as nitinol. Other materials may also be used such as stainless steel.

In operation, stent 40 is deformed either by inducing stress, or in the case of a shape memory alloy not having stress induced martensite characteristics, reducing temperature sufficiently to reach the temperature threshold for the metal's martensitic phase. After deformation of stent 40, it is loaded within sheath introducer 45. Sheath introducer 45 is of standard material, and is comprised of a distal end and a proximal end (not shown), each end having an opening 48.

Stent 40 may also be passed over a balloon catheter 50 prior to deformation and pre-loading within sheath introducer 45, then loaded with balloon catheter 50. Balloon catheter 50 is comprised of a catheter 51 having a distal end 52 and a proximal end (not shown). In addition, catheter 51 is comprised of an opening at proximal end (not shown) and an opening into balloon (not shown) which is integral with distal end 52. Balloon catheter 50 is further comprised of an opening 57 at distal end 52 for passage of catheter 50 over guide wire 21.

Stent delivery system is further comprised of standard plunger having a central lumen for passage over catheter 51, and a head for contact with stent 40 at a substantially flat surface of the plunger during stent deployment. Head is comprised of a standard substantially rigid material such as plastic or metal located at the forward most part of plunger for pushing force during deployment of stent 40.

In operation, the present invention is comprised of the following steps. First, strings 12 are temporarily attached to loops 11 of graft 10 by passing ends 14 through loops 11 and folding strings 12 over at middle portion 13 such that the string ends 14 are extending away from graft 10 at the same length. Graft 10 is then loaded into sheath introducer 15 such that string ends 14 are extending outward from each sheath opening 20. For loading of graft 10 into sheath introducer 15, graft 10 may be either twisted or folded so that the entry diameter is small.

Figure 4:
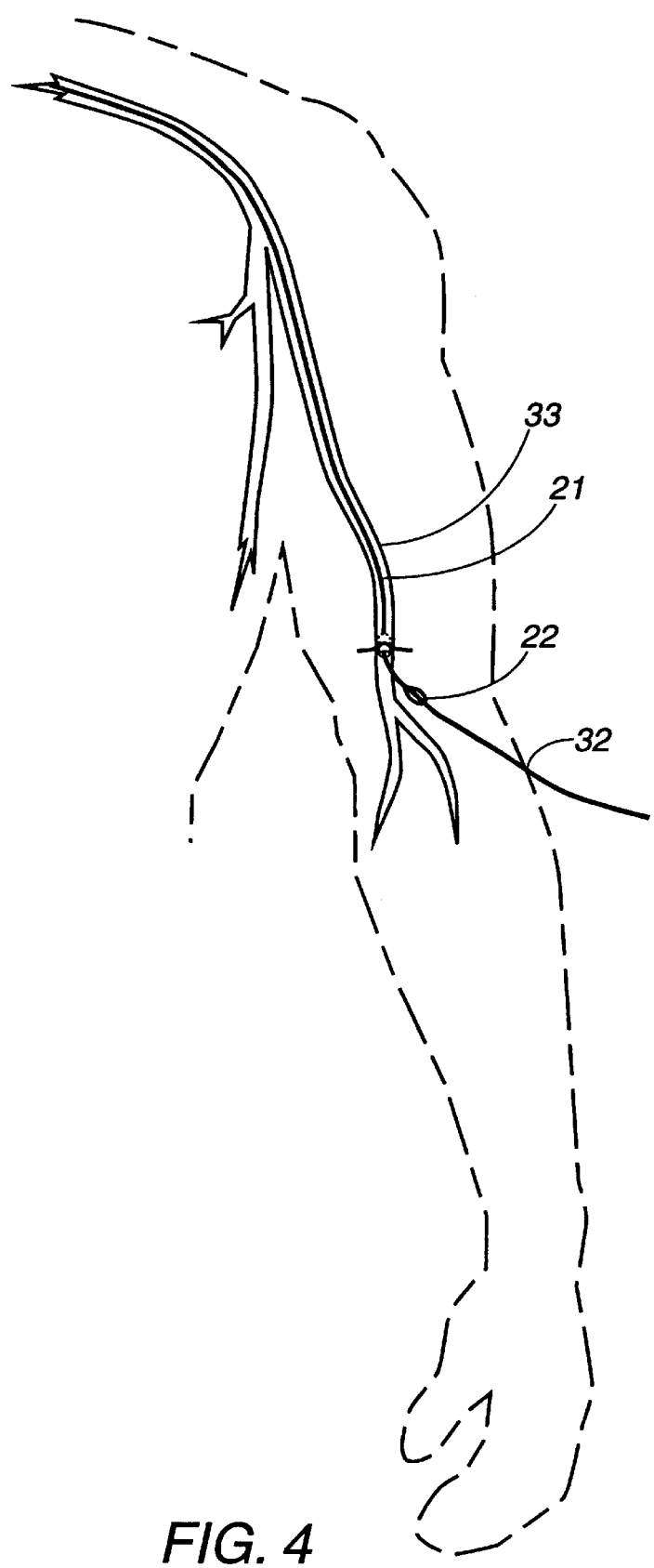
FIG. 4 is a perspective view of the guide wire of the present invention entering the brachial artery.
Figure 5:
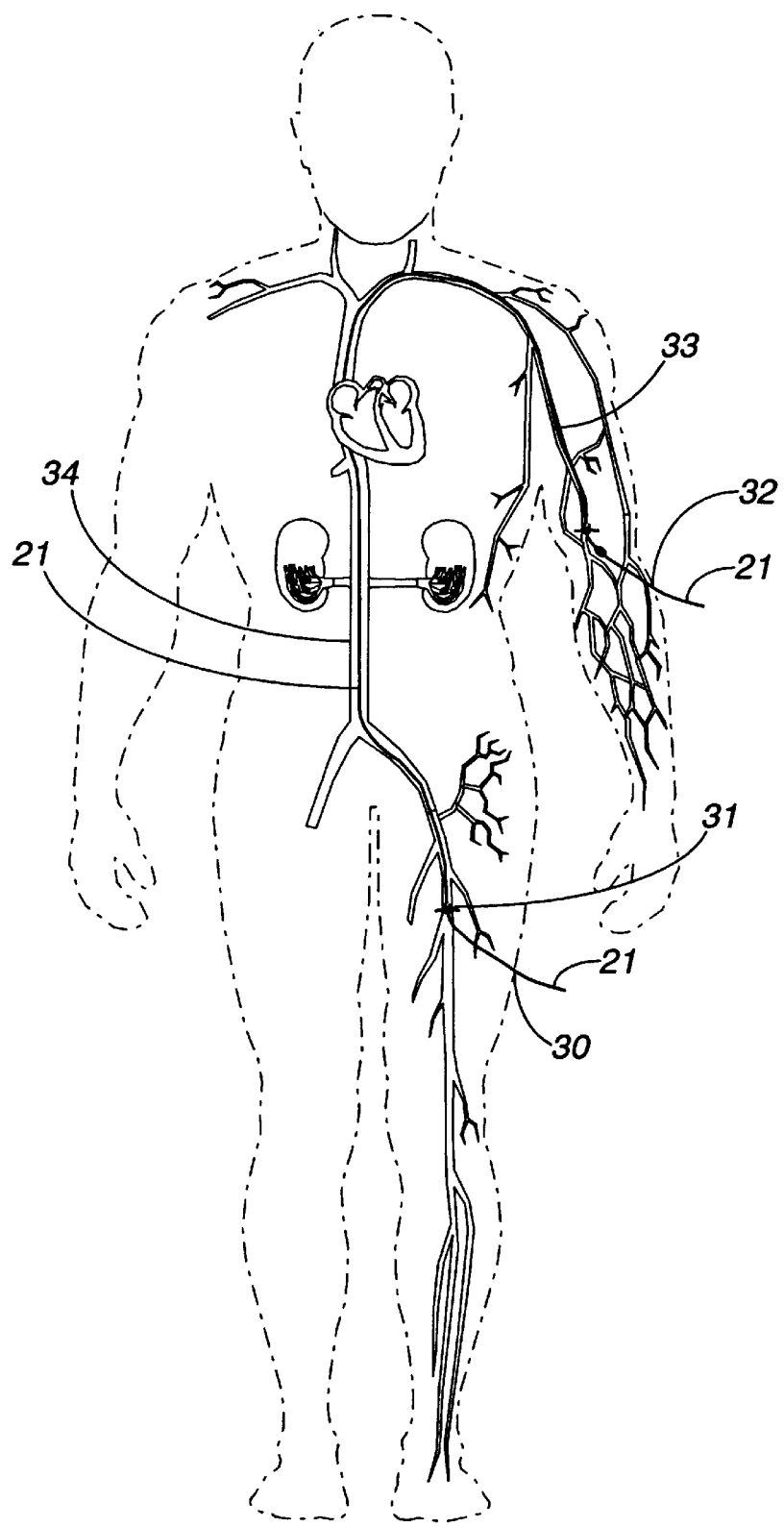
FIG. 5 is a perspective view of the guide wire of the present invention passing between the brachial artery and the femoral artery and exiting the femoral artery.
Figure 6A:
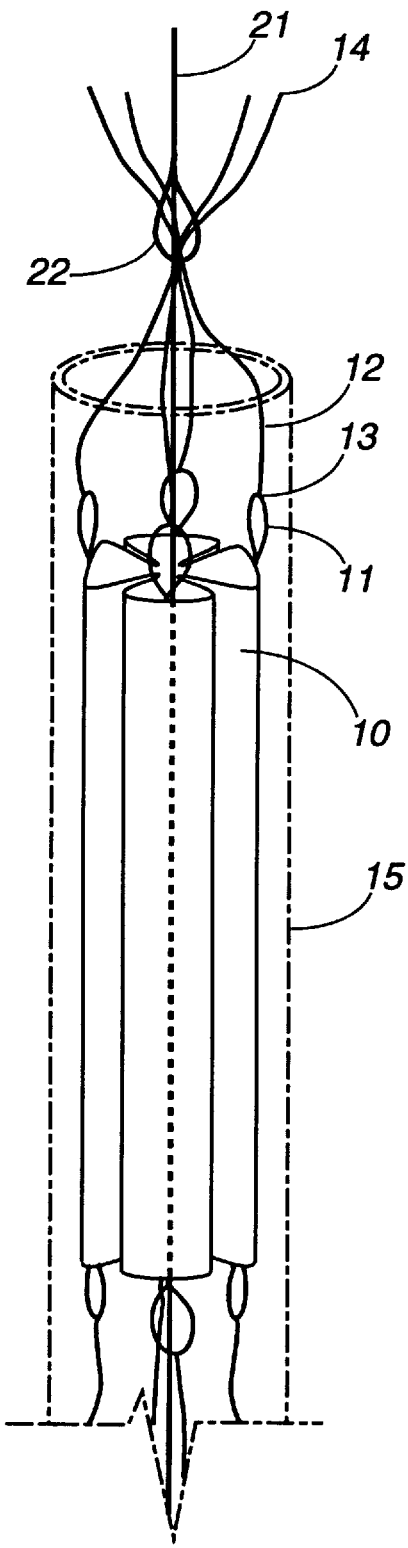
FIG. 6A is a perspective view of the first embodiment of the guide wire attached to the strings of the present invention.
Figure 6B:
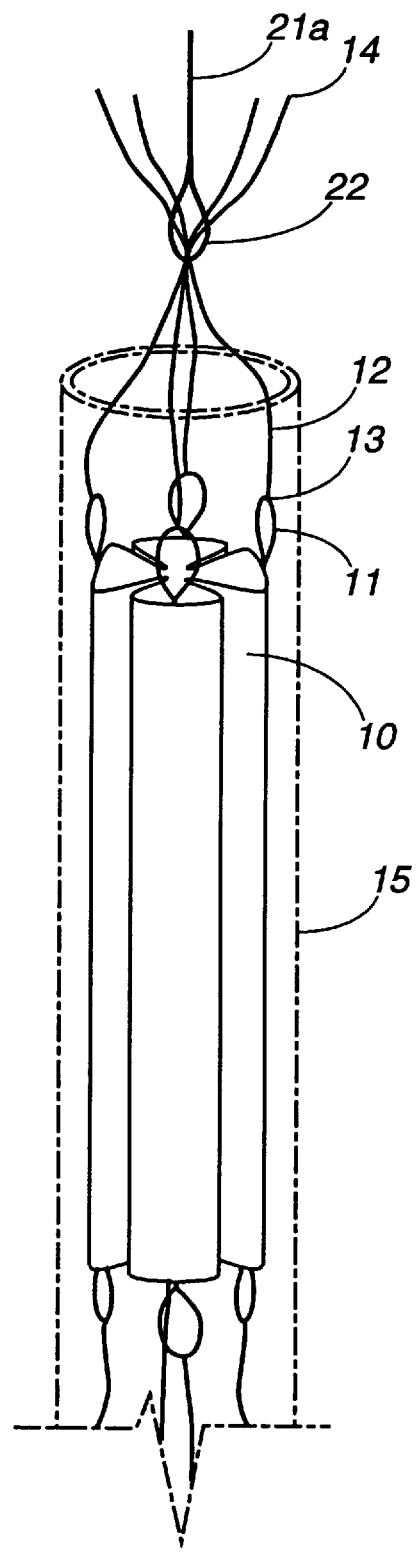
FIG. 6B is a perspective view of the second embodiment of the guide wire attached to the strings of the present invention.
Figure 7:
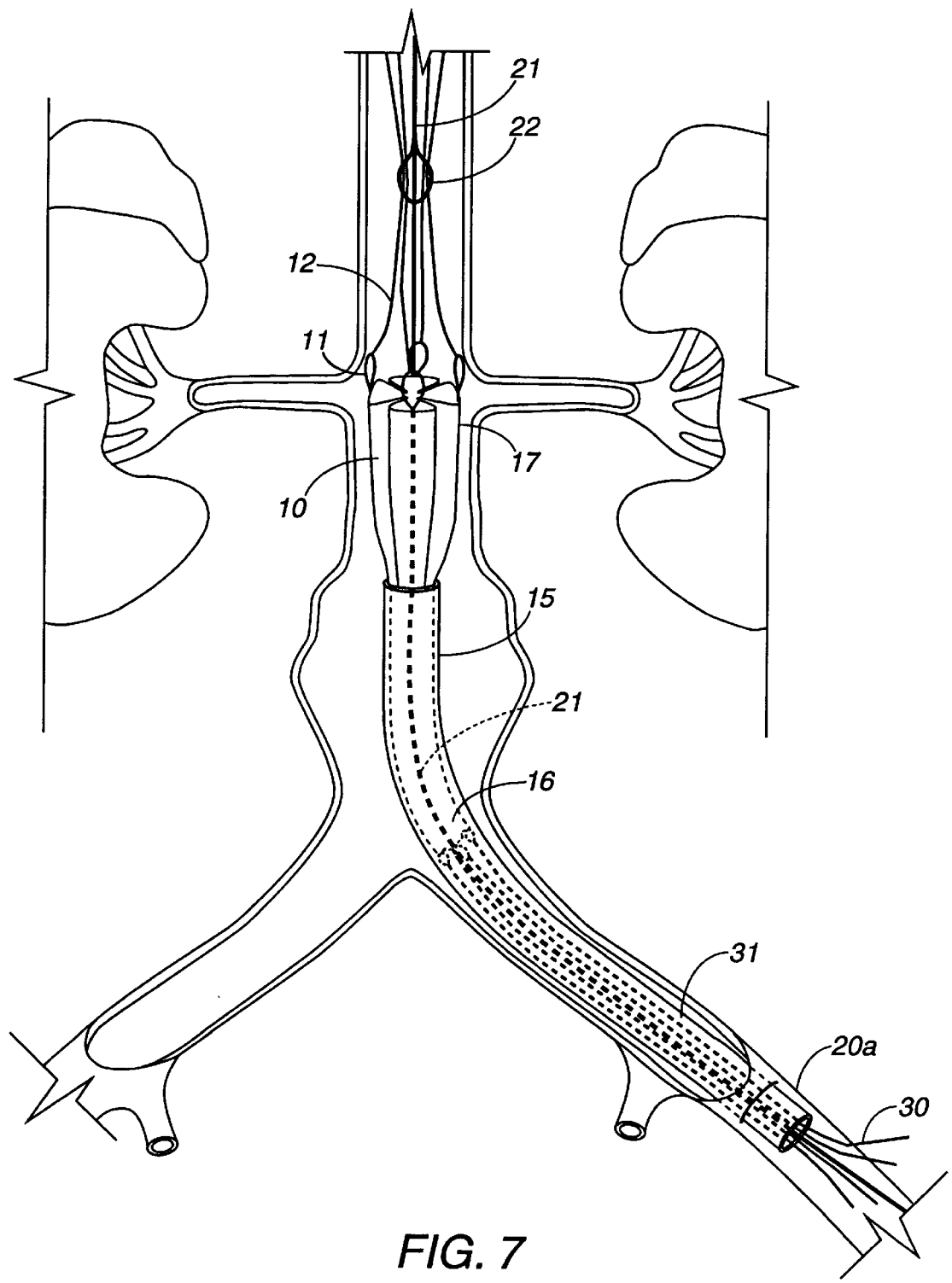
FIG. 7 is a perspective view of the sheath introducer of the present invention and the graft exiting therefrom into the vessel in the region of the aneurysm.
Figure 8:
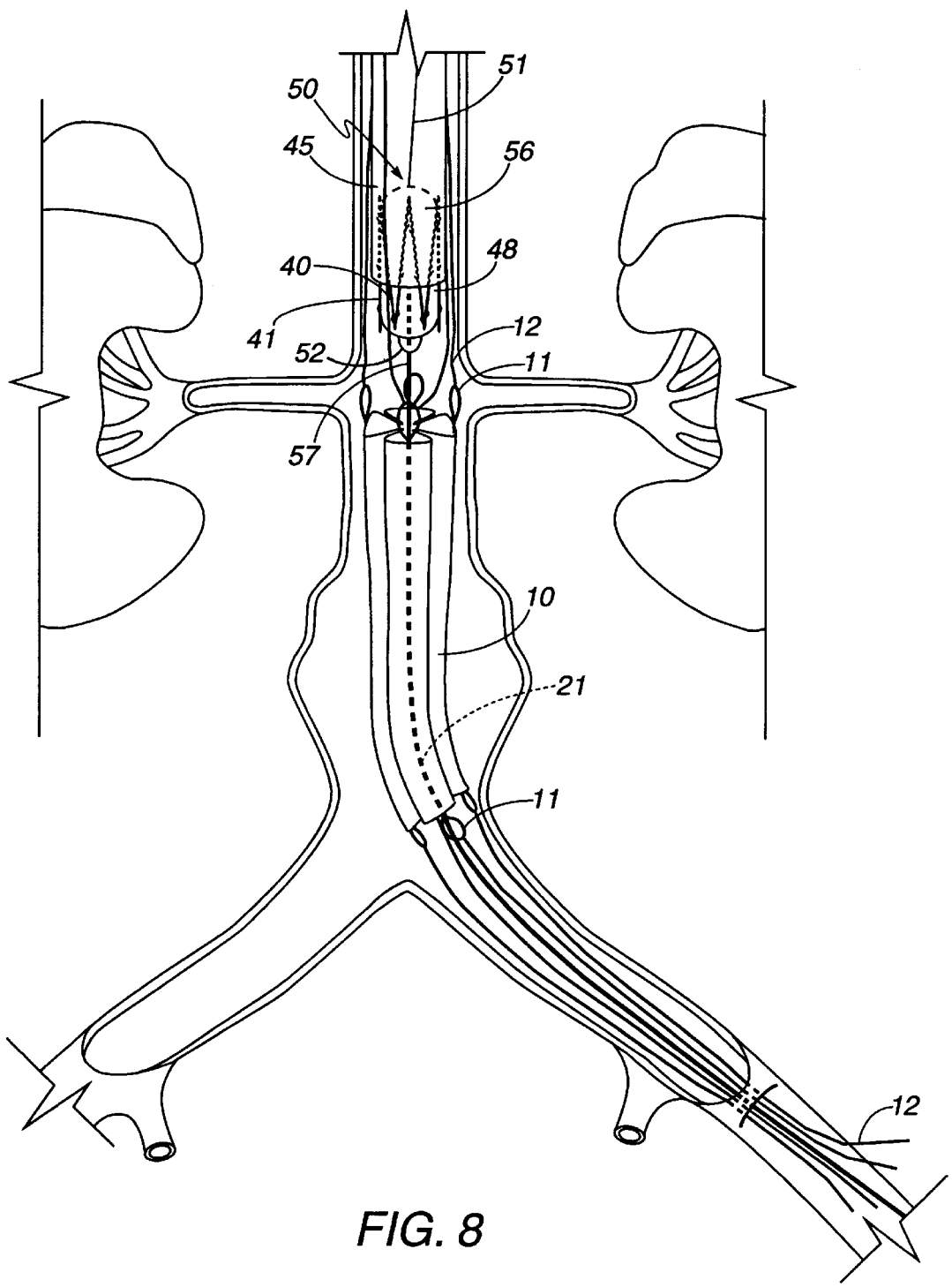
FIG. 8 is a perspective view of the graft of the present invention within the blood vessel and the stent deployment system being moved into position for stent deployment.
Figure 9:
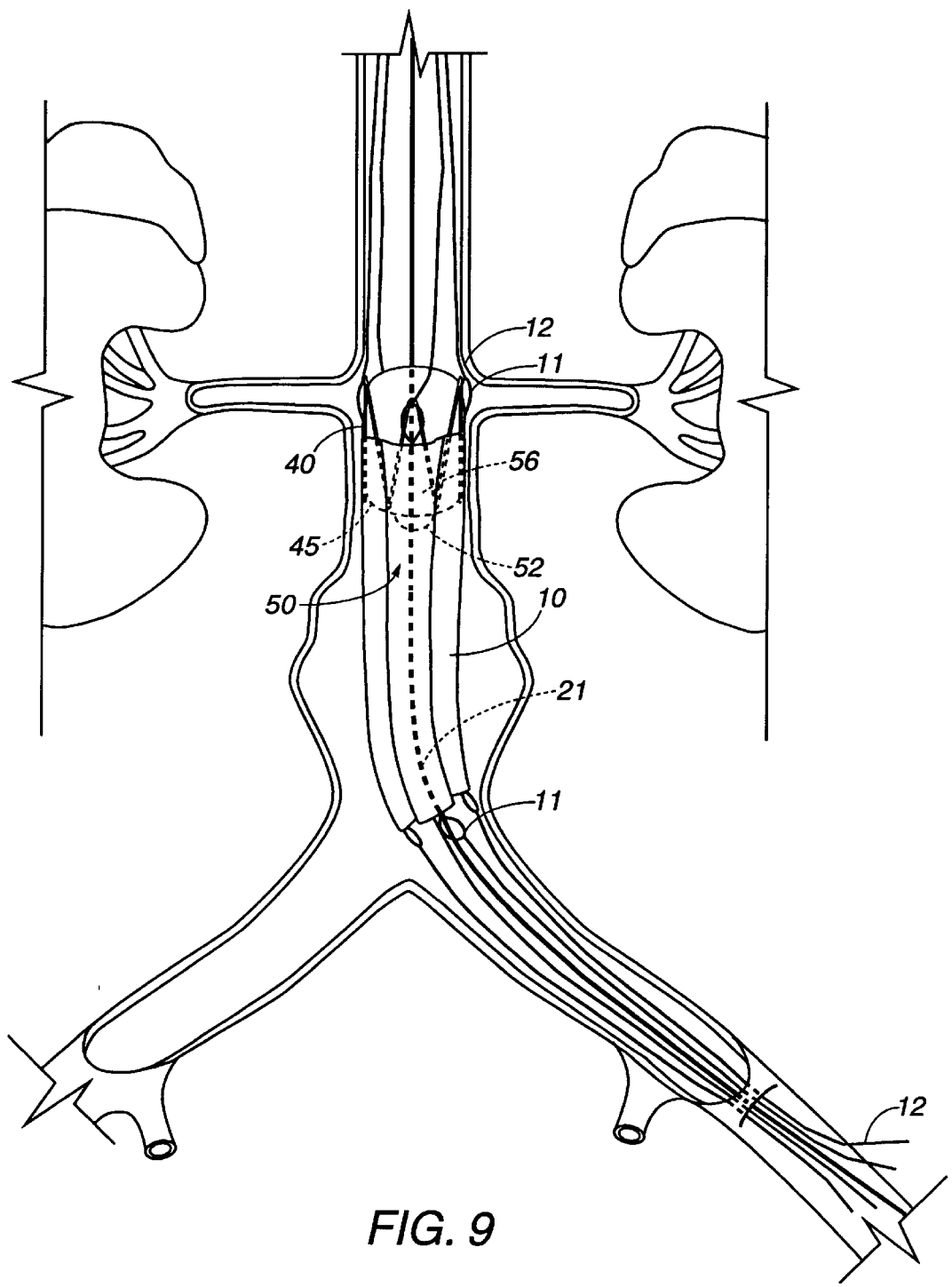
FIG. 9 is a perspective view of a stent being deployed into the graft of the present invention.
Figure 10:
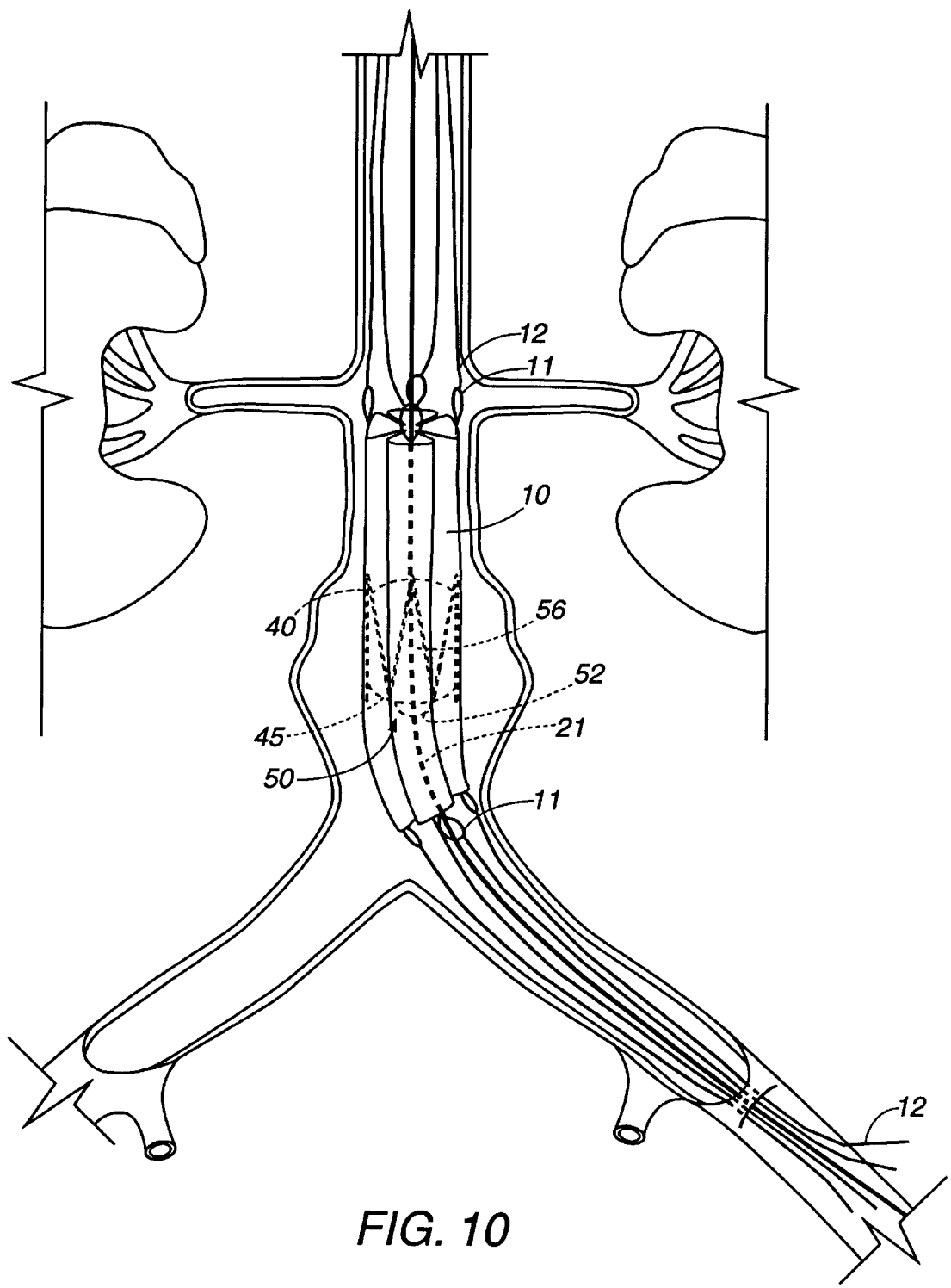
FIG. 10 is a perspective view of a stent being deployed into the graft of the present invention.
Figure 11:
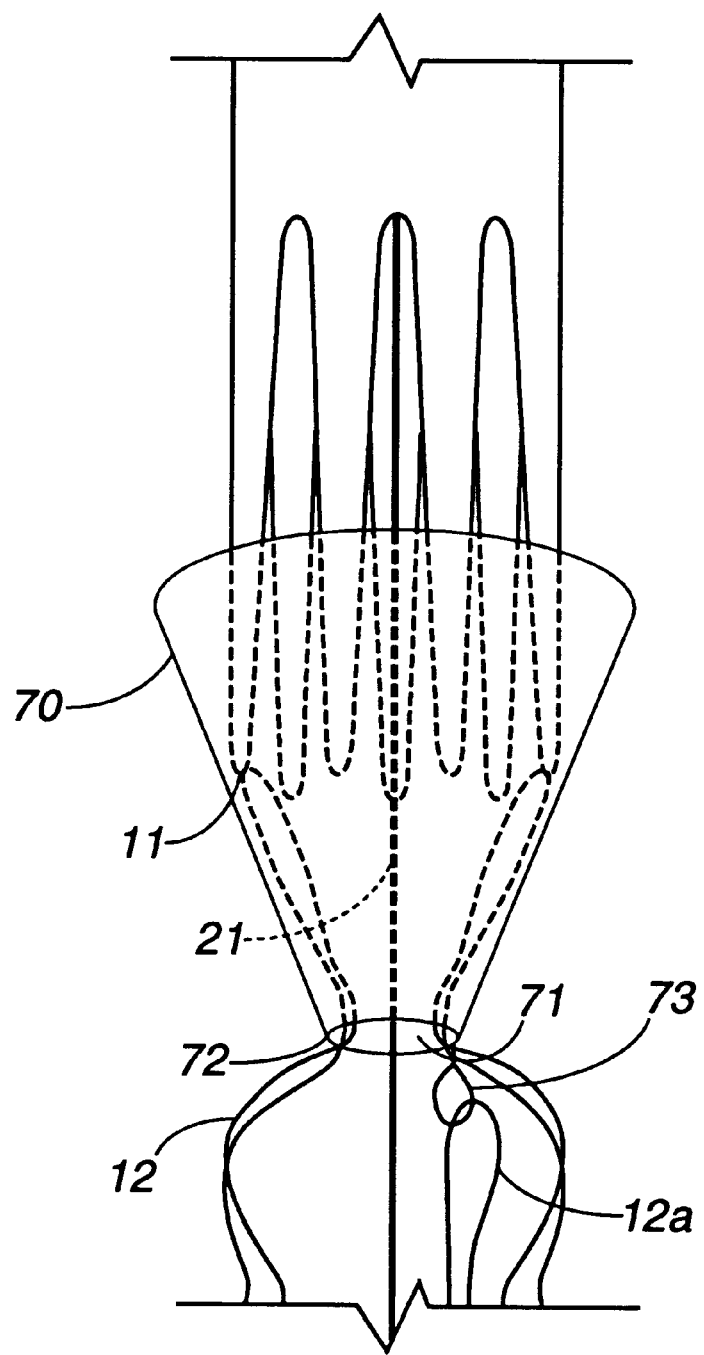
FIG. 11 is a perspective view of the end cap of the present invention engaged with the graft, strings, and guide wire.
Figure 12:
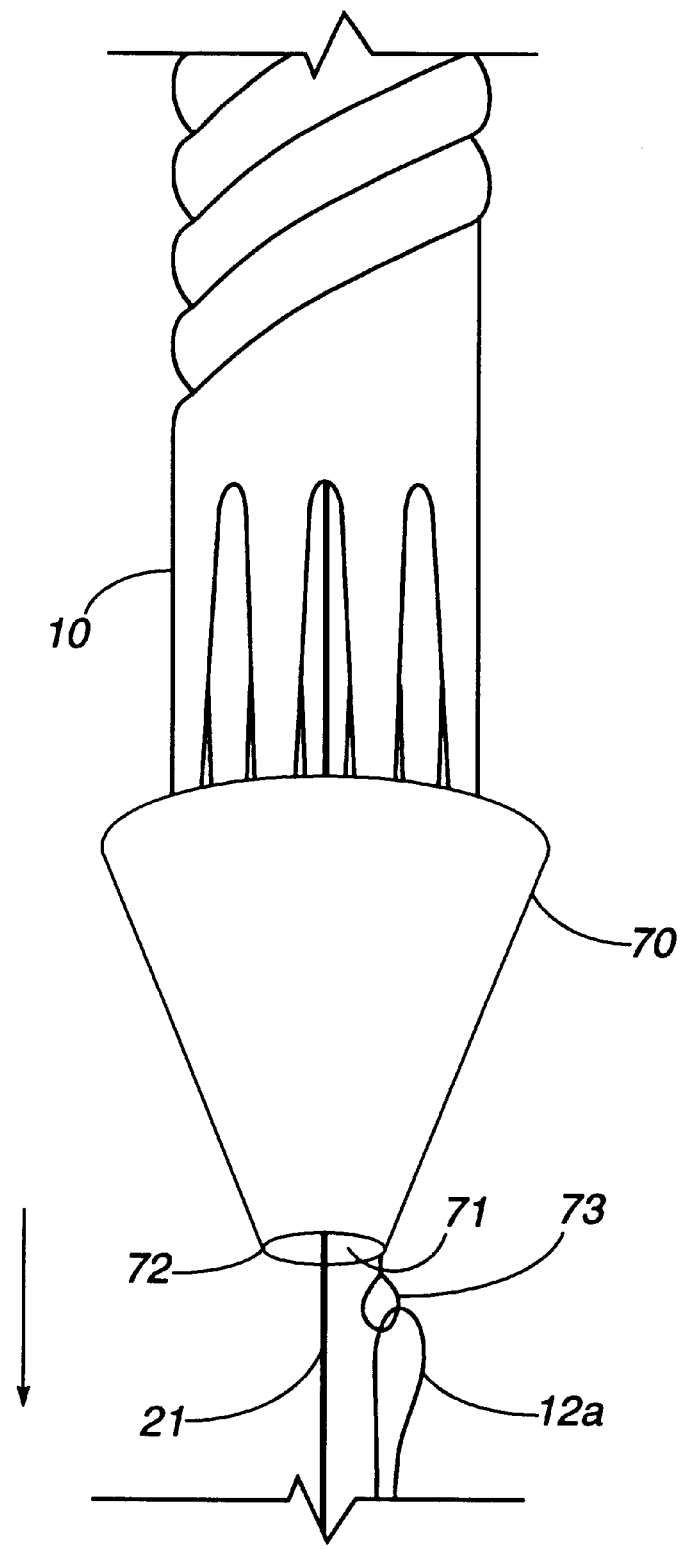
FIG. 12 is a perspective view of the end cap of the present invention engaged with the graft, strings, and guide wire.
Figure 13:
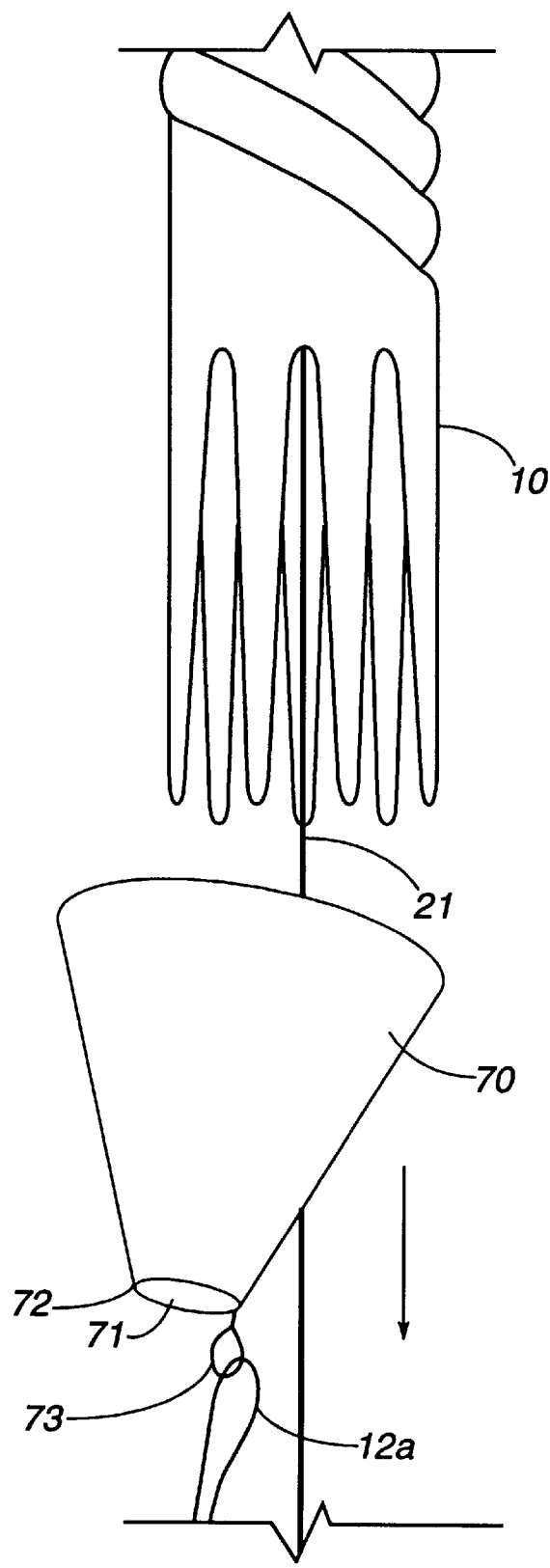
FIG. 13 is a perspective view of the end cap of the present invention being removed from the graft.
Figure 14:
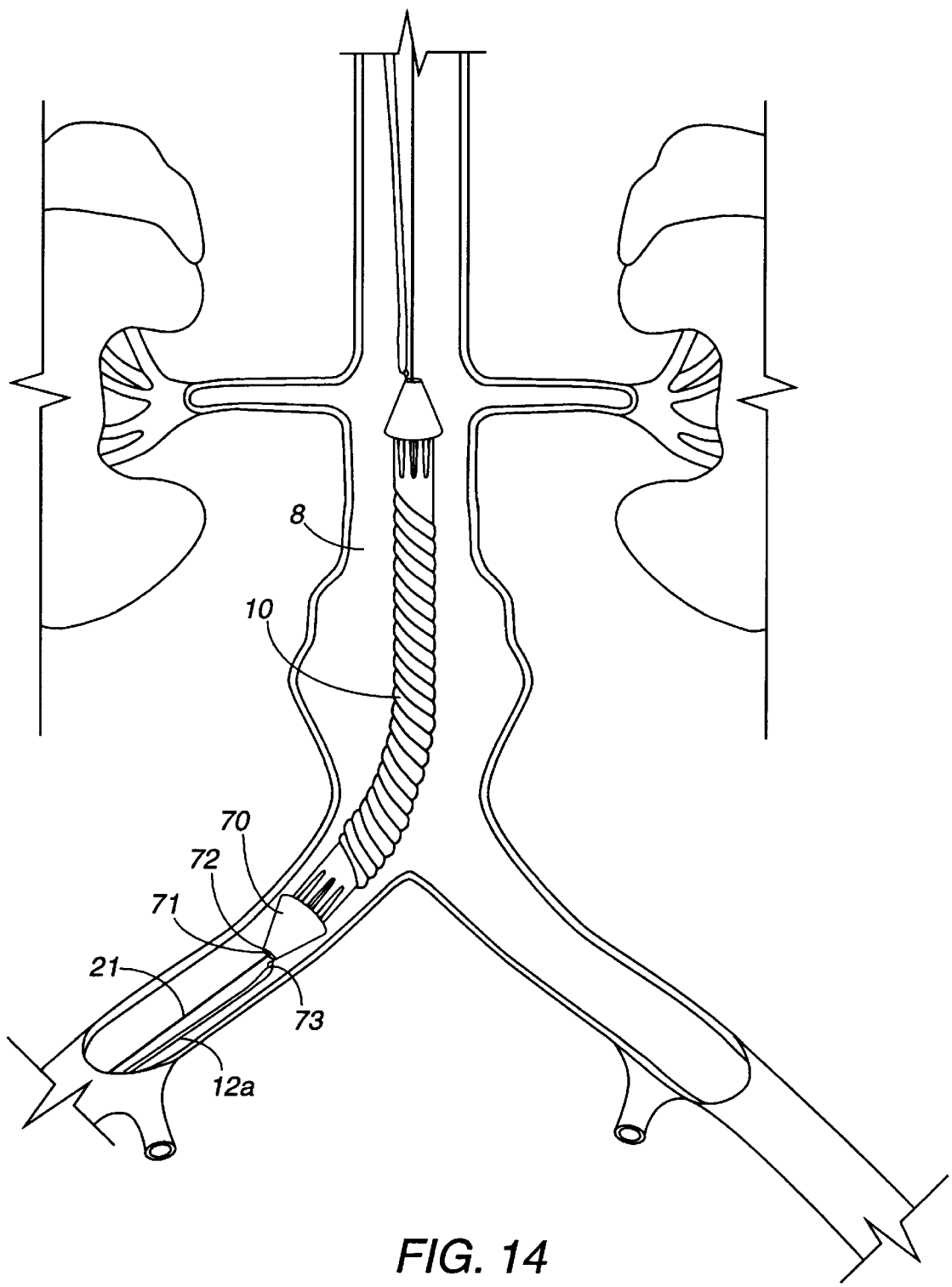
FIG. 14 is a perspective view of both end caps of the present invention engaged with the both graft ends, strings, and guide wire.
Figure 15:
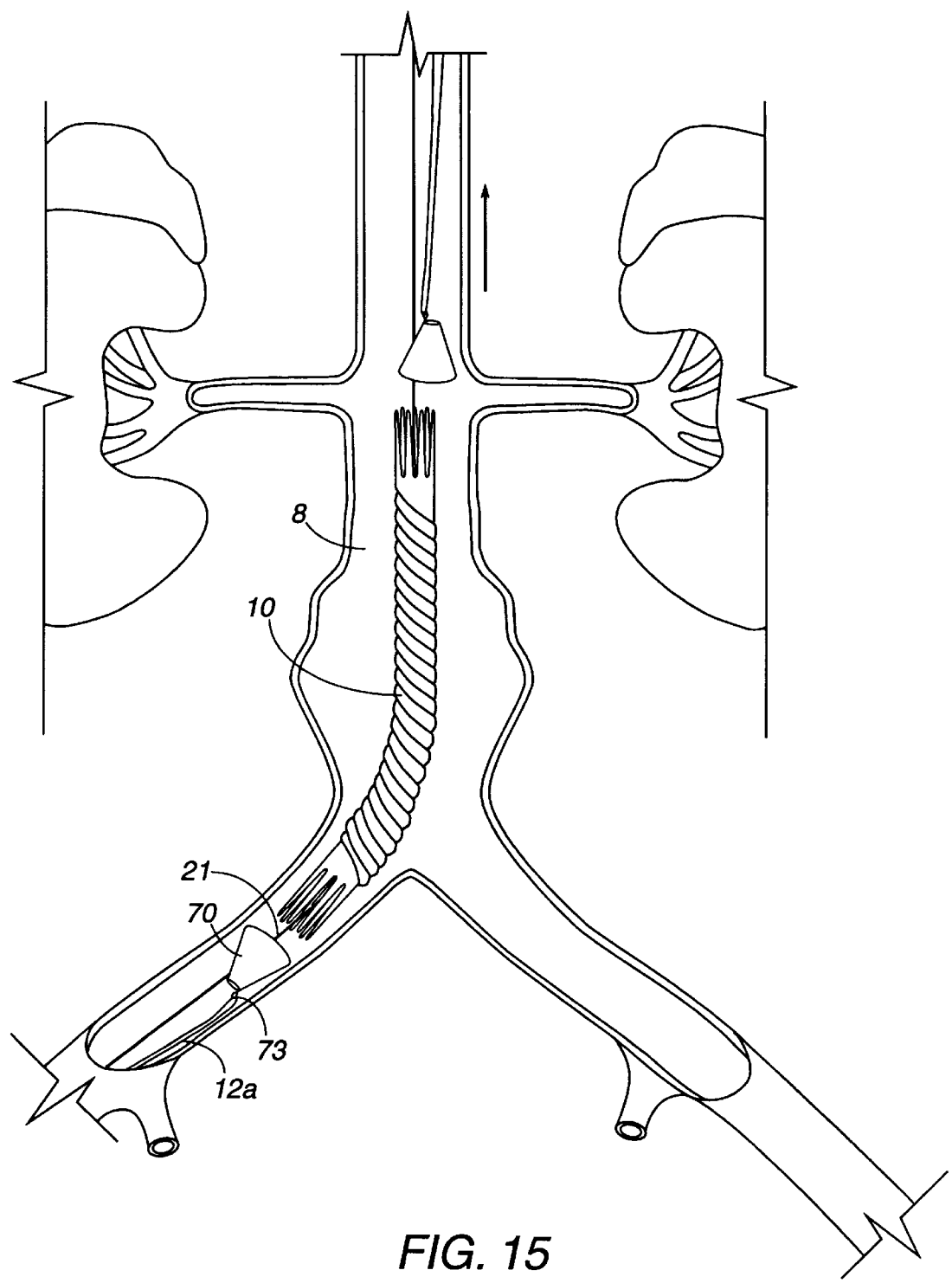
FIG. 15 is a perspective view of both end caps of the present invention being removed from the graft.

Next, as depicted in FIGS. 4 and 5, guide wire 21 is inserted into the brachial artery 33 at point of entry 32, passed through the descending aorta 34, into the femoral artery 31, and passed out of the vessel at point of entry 30. Guide wire 21 is then pulled from point of entry 30 until attachment means 22 emerges from the femoral artery 31.

String ends 14 at second end 17 of graft 10 are attached temporarily to attachment means 22 of guide wire 21. Distal end 27 of guide wire 21 is passed through opening 20 of sheath introducer and through the central lumen (not shown) of graft 10. By virtue of the length of guide wire 21, distal end 27 will extend through graft 10 and exit at the proximal opening 20a of sheath introducer 15.

After string ends 14 have been temporarily attached to attachment means 22, guide wire 21 may be withdrawn from point of entry 32 until attachment means 22 and string ends 14 have been withdrawn completely from vessel 33 and may be manipulated by hand. Guide wire 21 may then be cut at a point distal attachment means 22 so that guide wire 21 may be used to guide stent deployment apparatus to the appropriate point in vessel 34.

String ends 14 may then be used to assist movement of sheath introducer 15 through the vessels to a point within vessel 34 of the aneurysm site using an image amplifier. The position of graft 10 can be verified, and sheath introducer 15 may then be withdrawn from vessel, thus deploying graft 10 within vessel 34. String ends 14 may be used to hold graft 10 in position from both points of entry 32 and 30.

With graft 10 in position, stent deployment apparatus may be inserted into brachial artery 33, passed over guide wire 21 until its distal end 46 is within second end 17 of graft 10. At the appropriate position, sheath introducer 45 may be withdrawn, while at the same time applying pushing pressure to plunger for deployment of stent 40 within second end 17 of graft 10. After stent 40 is deployed and expanded within graft 10, balloon 56 of balloon catheter 50 may be expanded to secure the position of stent 40 within graft 10 and firmly affix spikes 41 within both graft 10 and vessel 34. After the position of stent 40 is secure, balloon 56 of balloon catheter 50 may be deflated and the deployment apparatus removed from the vessel.

With guide wire 21 still in position, additional stents 40 may be deployed in the same manner within graft 10 until graft 10 is sufficiently secured to vessel wall 34. It is generally necessary to deploy at least two stents 40 within graft 10; one on each side of aneurysm 8. It is also valuable to deploy a stent into the middle of graft 10 to support the lumen thereof. If sufficient space is available for affixing stents 40 to graft 10 and vessel wall 34, three or more stents 40 may be used to secure graft 10 thereto. Since guide wire 21 extends from point of entry 30 to point of entry 32, the stent deployment apparatus may be used from either point of entry to deploy stents 40 within graft 10.

After stents 40 have been deployed within graft 10, and the stent deployment apparatus has been removed from the vessel, strings 12 may be removed by pulling one end 14 of each string until its opposing end is fully withdrawn from the vessel.

Entry sites may then be attended.

As shown in FIGS. 11–15, an alternative embodiment provides an even smaller entry profile. End caps 70 may be used in place of sheath introducer 15 for restraining graft 10 during deployment thereof. Prior to insertion of graft 10 into a vessel, graft 10 is twisted and each end is placed within an end cap 70.

End caps 70 are preferably comprised of silicon, and are of a cone shape with an opening 71 at the tip 72 thereof. Opening 71 enables end cap 70 to pass over guide wire 21 through vessels. Opening 71 further enables passage of strings 12 through to attachment means 22. In addition, end cap 70 is comprised of a cap ring 73 to facilitate the temporary attachment of string 12*a* thereto, just as strings 12 are attached to graft loops 11, and for the removal of end cap 70 after successful positioning of graft 10. After temporary attachment of string 12*a* to cap ring 73, ends of string 12*a* are attached to attachment means 22 of guide wire 21, along with string ends 14, for passage through the vessels.

In operation, after graft ends are loaded into end caps 70, and guide wire 21 is withdrawn sufficiently such that string ends 14 and 14*a* are removed from vessel at initial point of entry 30 of guide wire 21, graft 10 is inserted into vessel over guide wire 21, and pulled through vessel to the aneurysm site by string ends 14. Care must be taken, however, not to prematurely tug on string ends 14*a* or end cap 70 will be prematurely removed from graft 10.

Graft 10 is pulled into the position for deployment and verified with an image amplifier. When positioned, string ends 14a are pulled to remove end caps 70 from each side of graft 10. By continuing to pull on string ends 14*a*, end caps 70 may be removed from the vessels.

Stent delivery apparatus may then be used as described hereinabove to deploy stents 40 within graft 10.

What is claimed is:

1. An assembly for positioning a graft within a vasculature, which comprises:

a) a guide wire having proximal and distal ends and a first attachment portions wherein the guide wire has a length between the ends sufficient to extend from an entry opening into the vasculature, past a treatment zone and out an exit opening from the vasculature;

b) a graft having a central lumen extending to proximal and distal graft ends; and c) at least one string extending from each of the proximal and distal graft ends, wherein the at least one string extending from the distal graft end is connectable to the first attachment portion of the guide wire so that when the guide wire extends through the vasculature with the proximal end thereof extending out the entry opening and with the first attachment portion accessible from outside the vasculature adjacent to the entry opening, the at least one string extending from the distal graft end is connectable to the first attachment portion so that the guide wire is manipulatable to move the graft through the vasculature until the at least one string extending from the distal graft end and connected to the first attachment portion of the guide wire extends out the exit opening and the at least one string extending from the proximal graft end extends out the entry opening, and wherein the at least one string extending from the distal draft end is disconnectable from the first attachment portion of the guide wire to remove the guide wire from connection with the graft so that the graft is positionable to span the treatment zone by manipulation of the at least one string connected to each of the proximal and distal graft ends.

2. The assembly of claim 1 further including:

(a) a catheter having proximal and distal ends and an expandable balloon provided at a distal portion of the catheter; and (b) an expandable stent mounted on the expandable balloon of the catheter, wherein the catheter is movable along the vasculature from either the entry opening or the exit opening to a position at least partially inside the lumen of the graft so that when the expandable balloon is expanded, the expandable stent secures the graft to an inner wall of the vasculature.

3. The assembly of claim 2 wherein the expandable catheter is manipulatable to secure the graft to the inner wall of the vasculature on either side of the treatment zone.

4. The assembly of claim 2 wherein the graft is initially provided in a radially reduced state until such time as the stent secures the graft to the inner wall of the vasculature.

5. The assembly of claim 1 wherein the graft has at least one second attachment portion provided at each of the proximal and distal ends thereof.

6. The assembly of claim 5 wherein at least one string is connectable to the second attachment portion at both the proximal and distal graft ends to provide at least one string extending from the proximal and distal graft ends.

7. The assembly of claim 5 wherein the second attachment portions provided at the proximal and distal graft ends are graft loops-and wherein the at least one string is connectable to the second attachment portion by moving the string through the loop and doubling the string back upon itself.

8. The assembly of claim 1 wherein when the guide wire extends through the vasculature with the proximal end thereof extending out the entry opening and with the first attachment portion accessible from outside the vasculature adjacent to the entry opening, the distal end of the guide wire extends out the exit opening from the vasculature.

9. The assembly of claim 1 further including a restraining device positioned on and about the craft as the graft is positionable to span the treatment zone.

10. The assembly of claim 9 wherein the restraining device is a cylindrically-shaped sheath introducer provided along and about the graft as the graft is positionable to span the treatment zone.

11. The assembly of claim 1 wherein the location of the graft in the vasculature is verifiable by an image amplifier.

12. The assembly of claim 1 further including a restraining device positioned on the at least one string extending from the distal end of the graft to the first attachment portion of the guide wire, wherein the restraining device is an end cap provided adjacent to the distal end of the graft.

13. The assembly of claim 12 wherein the end cap is cone shaped.

14. The assembly of claim 12 wherein the end cap is comprised of a cap ring.

15. The assembly of claim 1 wherein the graft further comprises a plurality of second attachment portions at both the proximal and distal graft ends to provide a plurality of strings extending from both the proximal and distal graft ends.

16. The assembly of claim 11 further comprising a catheter and a plunger movably positioned within a lumen of the catheter for securing the graft to the inner wall of the vasculature with the stent moved into position by the catheter.

17. The assembly of claim 1 further comprising an entry sheath for maintaining the patency of the entry opening and the exit opening.

18. The assembly of claim 1 wherein the guide wire is comprised of a middle portion, and the first attachment portion is comprised of a ring located at the middle portion of the guide wire.

19. The assembly of claim 1 wherein the first attachment portion is a ring positioned at the distal end of the guide wire.

20. The assembly of claim 1 wherein the guide wire is less than 0.38 millimeters in diameter.

21. The assembly of claim 5 wherein the second attachment portions provided at the proximal and distal graft ends are comprised of one or more graft loops.

22. An assembly for repairing an aneurysm within a vasculature, which comprises:
 a) a guide wire having proximal and distal ends and a first attachment portion, wherein the guide wire has a length between the ends sufficient to extend from an entry opening into the vasculature, past a treatment zone and out an exit opening from the vasculature;
 b) an engrafting device having a central lumen extending to proximal and distal ends thereof; and
 c) at least one string extending from each of the proximal and distal ends of the engrafting device, wherein the at least one string extending from the distal end of the engrafting device is connectable to the first attachment portion of the guide wire so that when the guide wire extends through the vasculature with the proximal end thereof extending out the entry opening and with the first attachment portion accessible from outside the vasculature adjacent to the entry opening, the at least one string extending from the distal end of the engrafting device is connectable to the first attachment portion so that the guide wire is manipulable to move the engrafting device through the vasculature until the at least one string extending from the distal end of the engrafting device and connected to the first attachment portion of the guide wire extends out the exit opening and the at least one string extending from the proximal end of the engrafting device extends out the entry opening, and wherein the at least one string extending from the distal end of the engrafting device is disconnectable from the first attachment portion of the guide wire to remove the guide wire from connection with the engrafting device so that the engrafting device is positionable to span the aneurysm by manipulation of the at least one sting connected to each of the proximal and distal ends of the engrafting device.

23. An assembly for positioning a stent within a vasculature, which comprises:
 a) a guide wire having proximal and distal ends and a first attachment portion, wherein the guide wire has a length between the ends sufficient to extend from an entry opening into the vasculature, past a treatment zone and out an exit opening from the vasculature;
 b) a stent having a central lumen extending to proximal and distal ends thereof; and
 c) at least one string extending from each of the proximal and distal ends of the stent, wherein the at least one string extending from the distal end of the stent is connectable to the first attachment portion of the guide wire so that when the guide wire extends through the vasculature with the proximal end thereof extending out the entry opening and with the first attachment portion accessible from outside the vasculature adjacent to the entry opening, the at least one string extending from the distal end of the stent is connectable to the first attachment portion so that the guide wire is manipulable to move the stent through the vasculature until the at least one string extending from the distal end of the stent and connected to the first attachment portion of the guide wire extends out the exit opening and the at least one string extending from the proximal end of the stent extends out the entry opening, and wherein the at least one string extending from the distal end of the stent is disconnectable from the first attachment portion of the guide wire to remove the guide wire from connection with the stent so that the stent is positionable in the vasculature at a desired location by manipulation of the at least one string connected to each of the proximal and distal ends of the stent.

\* \* \* \* \*